(12) United States Patent
Caro

(10) Patent No.: US 7,338,506 B2
(45) Date of Patent: *Mar. 4, 2008

(54) SCLERAL CLIP AND PROCEDURES FOR USING SAME

(76) Inventor: Nicholas C. Caro, 2310 Iroquis Dr., Glenview, IL (US) 60025

( * ) Notice: Subject to any disclaimer, the term of this patent is extended or adjusted under 35 U.S.C. 154(b) by 159 days.

This patent is subject to a terminal disclaimer.

(21) Appl. No.: 10/250,840

(22) PCT Filed: Sep. 5, 2001

(86) PCT No.: PCT/US01/42018

§ 371 (c)(1),
(2), (4) Date: Oct. 20, 2003

(87) PCT Pub. No.: WO02/19925

PCT Pub. Date: Mar. 14, 2002

(65) Prior Publication Data

US 2004/0092968 A1    May 13, 2004

(51) Int. Cl.
*A61B 17/08* (2006.01)
(52) U.S. Cl. .................................................. 606/151
(58) Field of Classification Search ............... 606/142, 606/143, 151, 107; 623/11.11, 4.1, 905, 623/6.64; 128/898
See application file for complete search history.

(56) References Cited

U.S. PATENT DOCUMENTS

| | | | |
|---|---|---|---|
| 4,413,635 A | 11/1983 | Myer | |
| 4,414,985 A | 11/1983 | Myer | |
| 4,762,260 A | 8/1988 | Richards et al. | |
| 4,895,289 A | 1/1990 | Richards et al. | |
| 5,354,331 A | 10/1994 | Schachar | |
| 5,383,898 A * | 1/1995 | Sarfarazi | 606/214 |
| 5,465,737 A * | 11/1995 | Schachar | 128/898 |
| 5,489,299 A | 2/1996 | Schachar | |
| 5,503,165 A | 4/1996 | Schachar | |

(Continued)

FOREIGN PATENT DOCUMENTS

EP    0 386 361 A1    9/1990

OTHER PUBLICATIONS

Ronald A. Schachar, MD, PhD; Zonular Function: A New Hypothesis With Clinical Implications; Ann Ophthalmol 1994;26:36-38.*

(Continued)

*Primary Examiner*—Anhtuan T. Nguyen
*Assistant Examiner*—Tuan V. Nguyen
(74) *Attorney, Agent, or Firm*—Cook, Alex, McFarron, Manzo, Cummings & Mehler, Ltd.

(57) ABSTRACT

A method and clip for treating presbyopia and/or open angle glaucoma in which the sclera is supported or reinforced, while substantially maintaining the special relationship between the ciliary muscle and the lens. The method includes making an incision in the conjunctiva to gain access to the sclera overlying the ciliary muscle. The Tenon's capsules are moved laterally to expose the sclera, and the sclera is extended outwardly. A clip, or series of clips, is provided having two closeable arms for engaging the outwardly-extended sclera therebetween. The arms of the clip are closed on the sclera so as to grasp a portion of the sclera, and then the Tenon's capsules are slid over the clip and the conjunctiva is closed.

7 Claims, 3 Drawing Sheets

U.S. PATENT DOCUMENTS

| | | | |
|---|---|---|---|
| 5,529,076 | A | 6/1996 | Schachar |
| 5,609,599 | A | 3/1997 | Levin |
| 5,722,952 | A | 3/1998 | Schachar |
| 5,731,909 | A | 3/1998 | Schachar |
| 5,774,274 | A | 6/1998 | Schachar |
| 5,797,932 | A | 8/1998 | Min et al. |
| 6,007,578 | A * | 12/1999 | Schachar ................. 623/11.11 |
| 6,038,080 | A | 3/2000 | Schachar |
| 6,051,023 | A | 4/2000 | Kilmer et al. |
| 6,146,366 | A | 11/2000 | Schachar |
| 6,197,056 | B1 | 3/2001 | Schachar |
| 6,217,594 | B1 * | 4/2001 | Hallen et al. ............... 606/157 |
| 6,246,528 | B1 | 6/2001 | Schachar |
| 6,517,555 | B1 * | 2/2003 | Caro .......................... 606/151 |
| 6,673,111 | B2 | 1/2004 | Baikoff |
| 6,682,560 | B1 | 1/2004 | Baikoff |
| 6,692,524 | B2 | 2/2004 | Baikoff |
| 6,712,847 | B2 | 3/2004 | Baikoff et al. |
| 6,719,792 | B2 | 4/2004 | Baikoff |
| 2002/0019667 | A1 | 2/2002 | Baikoff |
| 2002/0026241 | A1 | 2/2002 | Baikoff |
| 2002/0035397 | A1 * | 3/2002 | Baikoff ....................... 623/4.1 |
| 2002/0138139 | A1 * | 9/2002 | Till ............................. 623/4.1 |
| 2002/0161433 | A1 | 10/2002 | Baikoff et al. |
| 2003/0033015 | A1 * | 2/2003 | Zhou et al. ................. 623/6.64 |
| 2003/0060748 | A1 | 3/2003 | Baikoff |
| 2004/0002756 | A1 | 1/2004 | Baikoff et al. |
| 2005/0197697 | A1 | 9/2005 | Baikoff et al. |

OTHER PUBLICATIONS

CLEARSIGHT, Inc., EP 01 96 8987 Supplementary European Search Report dated Aug. 24, 2004.

CLEARSIGHT, Inc., EP 01 96 8990 Supplementary European Search Report dated Aug. 24, 2004.

Mathews, Steven, "Scleral Expansion Surgery Does Not Restore Accommodation in Human Presbyopia," Opthalmology, vol. 106, No. 5, pp. 873-877 (1999).

Ronald A. Schachar, MD, PhD, "Cause and Treatment of Presbyopia With a Method for Increasing the Amplitude of Accommodation," Annals of Ophthalmology, vol. 24, No. 12, pp. 445-452 (1992).

Schachar et al., "In vivo increase of the human lens equatorial diameter during accommodation," American Physiological Society, pp. R670-R676 (1996).

Schachar et al., "The Effect of Gravity on the Amplitude of Accommodation," Annals of Ophthalmology, vol. 26, No. 3, pp. 65-70 (1994).

Ronald A.Schachar, MD, PhD, "Zonular Function: A New Hypothesis With Clinical Implications," Annals of Ophthalmology, vol. 26, No. 2, pp. 36-38 (1994).

Schachar et al., "A Physical Model Demonstrating Schachars's Hypothesis of Accommodation," Annals of Opthalmology, vol. 26, No. 1, pp. 4-9 (1994).

Schachar et al., "Experimental Support for Schachar's Hypothesis of Accommodation," Annals of Opthalmology, vol. 25, No. 11, pp. 404-409 (1993).

Ronald A. Schachar, MD, PhD, "Determination of Corneal Image-forming Properties From Corneal Topography," American Journal of Ophthalmology, Correspondence, vol. 115, No. 5, pp. 680-681 (1993).

Schachar et al., "Mathematic Proof of Schachar's Hypothesis of Accommodation," Annals of Ophthalmology, vol. 25, No. 1, pp. 5-9 (1993).

Internet Web Site, www. presbycorp.com/testindex.htm, ondated.

Neal A. Sher, MC, FACS, Surgery for Hyperopia and Presbyopia, Chapter 1, pp. 3-10; Chapter 4, pp. 33-36; Chapter 7, pp. 63-77; Chapter 20, pp. 195-199 (1997).

Package Labeling, Labtician Style 250, Corneal Clip (1995).

* cited by examiner

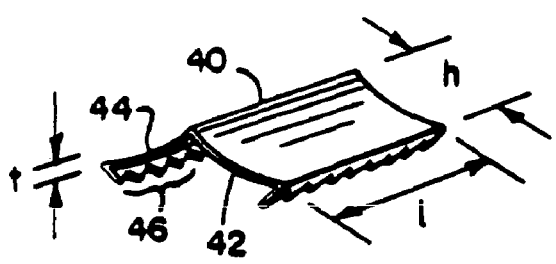
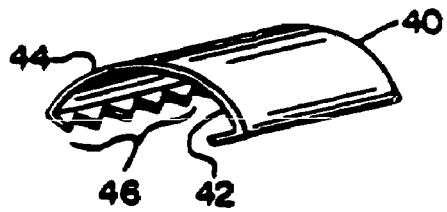
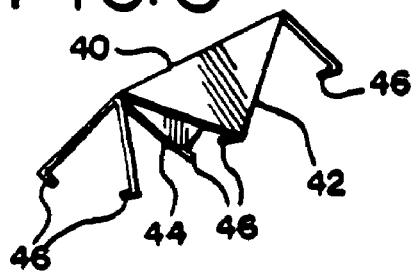
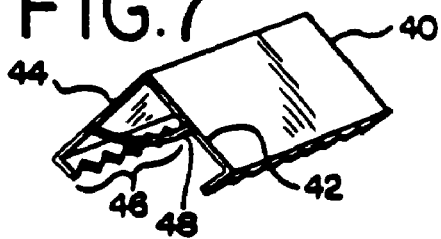
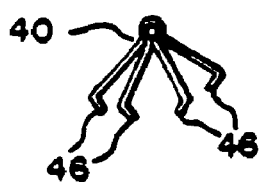
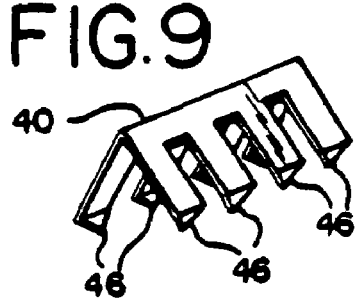
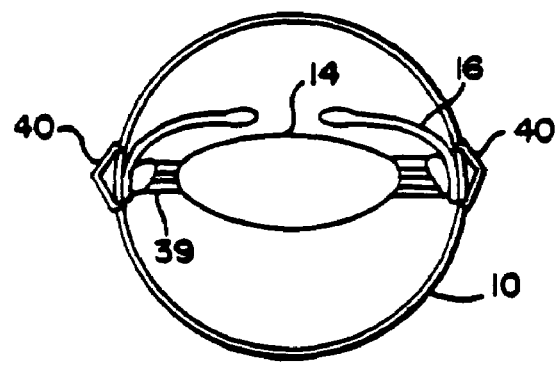

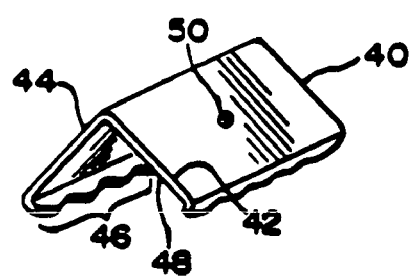
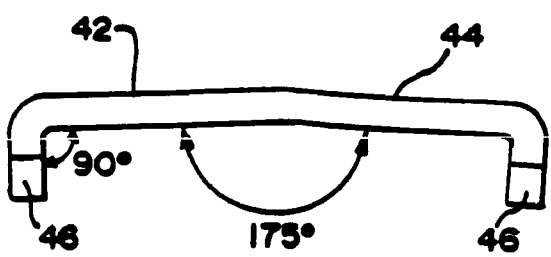
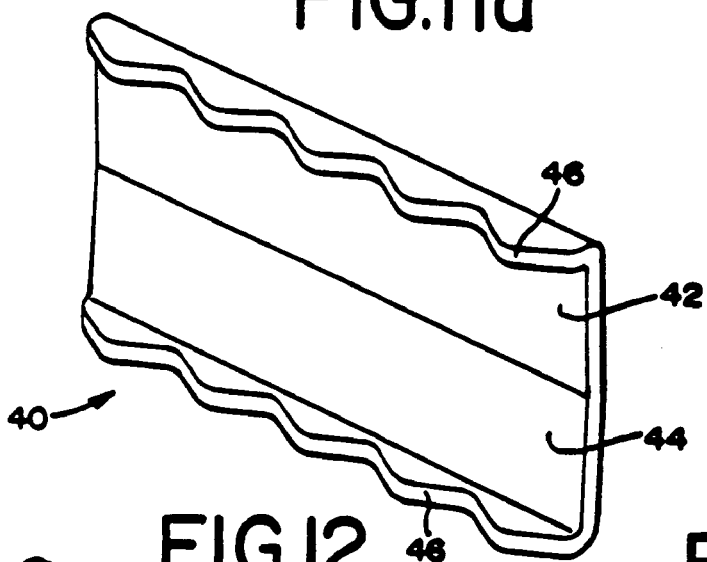
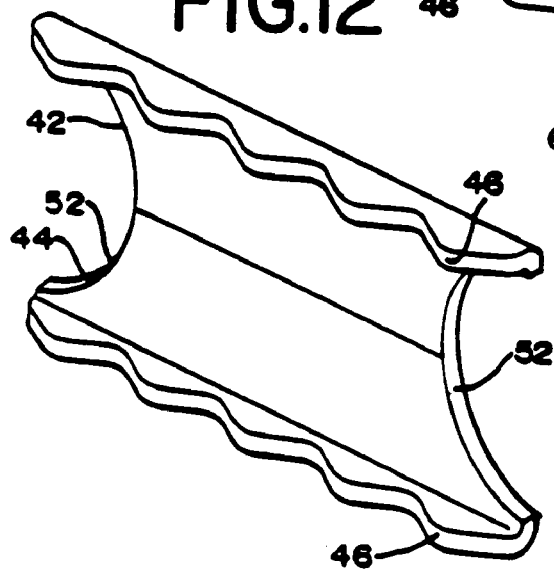
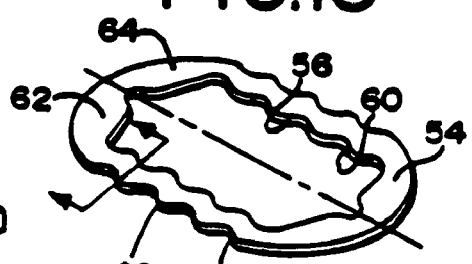
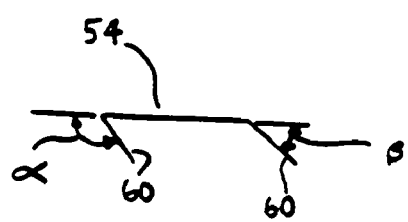

SCLERAL CLIP AND PROCEDURES FOR USING SAME

The present invention is directed to a surgical method for treating vision disorders, such as presbyopia and/or glaucoma, and to the associated devices used in conjunction with the method.

BACKGROUND OF THE INVENTION

Presbyopia is a vision disorder associated with aging resulting from the failure of the accommodation mechanism of the eye. The accommodative mechanism is driven principally by parasympathetic innervation of the ciliary smooth muscle. In the non-presbyopic eye, this causes the muscle to slide forward in a unified manner and produces an inward movement of the muscle. The result is a reduction in the diameter of the ciliary muscle collar that instigates a series of events leading to an ability to see near objects clearly.

While it is clear that the capsular elasticity of the lens of the eye, i.e., the ability of the lens capsule to mold the lens, diminishes with age, the precise cause of presbyopia remains the subject of debate.

Presbyopia is most frequently treated by the use of reading glasses, bifocals, and progressive multi-focal contact lenses. However, the inconveniences associated with eyeglasses and contact lenses have prompted investigation into, and the development of, surgical techniques aimed at correcting presbyopia.

One such method is anterior ciliary sclerotomy ("ACS"). ACS is based on the theory that accommodation results primarily from ciliary body contraction, with the resulting forward movement of the lens. Its underlying rationale is based on the observation that the lens constantly grows throughout life, gradually crowding the posterior chamber and eventually preventing full function of the ciliary body/zonular complex. The "crowded" state causes the reduction of lens power change with attempt at accommodation. ACS utilizes a series of symmetrical radial, partial-thickness scleral incisions to attempt to make more room for the ciliary body—which in turn allows more space for the lens—by expanding the globe in the area of the ciliary body. However, this procedure has many potential complications, ranging from infection and hemorrhaging to perforation, which could result in retinal detachment, iris injury or prolapse.

Another proposed method for surgical reversal of presbyopia is based on the theory that presbyopia results when the distance between the ciliary body and the equator of the lens and its capsule becomes less with age as a result of the normal growth of the lens. Thus, under this theory presbyopia is treated by increasing the effective working distance of the ciliary muscle. This is accomplished by implanting a series of scleral expansion bands just below the surface of the sclera and outside the cornea. The bands stretch the sclera so that the diameter of the circle describing the intersection of the plane of the ciliary body with the sclera is slightly increased. See, U.S. Pat. Nos. 5,354,331 and 5,489,299 to Schachar. However, at least one study has called into question the accuracy of the theory on which scleral expansion surgery is premised. See, Mathews, "Scleral Expansion Surgery Does Not Restore Accommodation in Human Presbyopia," Opthamology, Vol. 106, No. 5, May, 1999, pages 873-877. This study concludes that, if scleral expansion surgery does alleviate presbyopia, an explanation other than the restoration of accommodation needs to be found. Schachar also believes that his scleral expansion bands may have utility in the treatment of primary open-angle glaucoma by restoring the level of force which the ciliary muscle exerts on the trabecular meshwork, thus opening the drainage pores and relieving the intra ocular pressure (IOP).

Regardless of the theory employed, there is a need for correcting presbyopia without the use of eyeglasses or contact lenses through a relatively safe and simple procedure that is easily reversible. There is also a need for treating glaucoma that is safe, effective, and simple.

Accordingly it is the principal object of the present invention to provide a surgical method for the treatment of ophthalmic disorders that can be ameliorated by supporting or reinforcing the scleral.

More specifically, it is an object of the present invention to provide a surgical method for treating presbyopia and/or glaucoma.

It is a further object to provide such a method that has a reduced potential for complications and is easily reversible.

It is a still further object of the invention to provide a clip uniquely suited for use in the treatment of presbyopia and/or glaucoma.

SUMMARY OF THE INVENTION

These objects, as well as others which will become apparent upon reference to the following detailed description and accompanying drawings, are accomplished by a method for treating presbyopia and glaucoma in which the sclera is supported or reinforced, while the special relationship between the ciliary muscle and the lens is substantially unchanged. Specifically, the method includes making an incision in the conjunctiva to gain access to the sclera overlying the ciliary muscle. The Tenon's capsules are moved laterally to expose the sclera, and the sclera is extended outwardly. A clip, or series of clips, is provided for grasping the outwardly-extended sclera. The clip includes a series of teeth or similar structures that engage a portion of the sclera, thus securing the clip thereto, and then the Tenon's capsules are slid over the clip and the conjunctiva is closed. Preferably, four such scleral clips are applied to the sclera substantially equally spaced about the lens between the medial, inferior, lateral and superior rectus muscles. When applied to the sclera, the clips serve to prevent the sclera from buckling under tension applied by the ciliary muscle when trying to accommodate the eye to near vision.

In another aspect of the invention, a scleral clip is provided for applying to the sclera. The clips have a length of typically between 4 to 5 mm, and no longer than approximately 6.0 mm, so as to fit between adjacent rectus muscles. The clips are provided with means, such as teeth or spurs, for grasping—but not penetrating through—the sclera.

BRIEF DESCRIPTION OF THE DRAWINGS

FIG. 3 is a simplified diagram showing two scleral clips attached to an eye.

FIGS. 4-14 are views of clips of various configurations to be applied to the sclera in accordance with the present invention.

DETAILED DESCRIPTION

The method of the present invention is based upon a theory for the cause of presbyopia different from those set forth above. Specifically, presbyopia is caused by the failure of the ciliary body to adjust the lens diameter in order to focus images onto the retina for close objects. The ciliary muscles change the lens diameter by using the sclera as a support or fixation structure. As the sclera of the eye weakens due to age, the ciliary muscles lack the support needed in order to alter the lens diameter for focusing on close objects. Thus, in order to allow the ciliary muscle to alter the lens diameter to see close objects, the sclera must be supported or reinforced. Accordingly, a method is provided that utilizes a unique clip for reinforcing the sclera, so as to form a stronger and more stable support for the ciliary muscles. In effect, the sclera is strengthened, and the ciliary muscles are then able to again function properly to provide near vision.

It is believed that the method and its associated clip may also be advantageously used for the treatment of open angle glaucoma. Glaucoma, like presbyopia, is an age-related disease and is caused by a buildup of fluid pressure in the eye which damages the optic nerve. Over time, glaucoma destroys peripheral vision, thus shrinking the field of vision. In a healthy eye, the fluid produced by the ciliary tissues surrounding the lens is drained out of the eye by a series of drainage canals around the outer edge of the iris. With age, because the ciliary muscles lack support, they are less capable of maintaining these drainage canals in an open condition to allow free drainage of fluid. By tensioning the sclera according to the present method, the support is provided for the ciliary muscles, and the tissues of the eye that provide for drainage are stretched, thus reducing blockage of the fluid drainage canals and facilitating the drainage of fluid from the eye.

Figure 1:
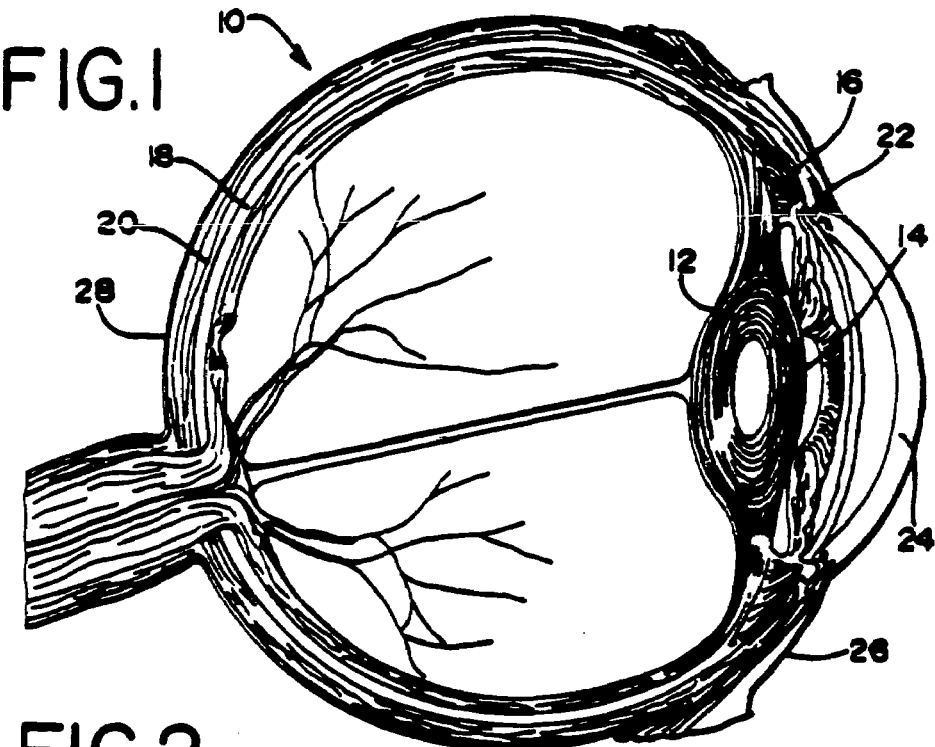
FIG. 1 is a horizontal sectional view of an eyeball.

With reference to FIG. 1, there is seen a simplified sectional view of a human eye 10 having a lens 12 contained within a lens capsule 14. The ciliary body and ciliary muscle 16 are connected to the lens capsule 14 and also to the choroid 18. The sclera 20 overlies the choroid 18 and, at the front of the eye, the ciliary muscles 16, and terminates in the scleral spur 22 at the cornea 24 of the eye. The conjunctiva 26 surrounds the cornea 24 and overlies the bulbar sheath (or Tenon's capsule) 28 which in turn, overlies the sclera 20 on the front of the eye 10. Blood is supplied to the sclera by arteries in the superior, inferior, medial and lateral rectus muscles 30, 32, 34, and 36 respectively, best seen in FIG. 2.

In the method of the invention, the eye is treated by first making a series generally linear incisions (such as incisions 38 in FIG. 2) in the conjunctiva 26 to gain access to the sclera 20. Preferably, prior to making the incisions, a generally standard preoperative procedure is performed that includes marking the limbus and cornea at 10:00, 2:00, 5:00 and 8:00 with violet blue to indicate the location of the incisions.

Figure 2:
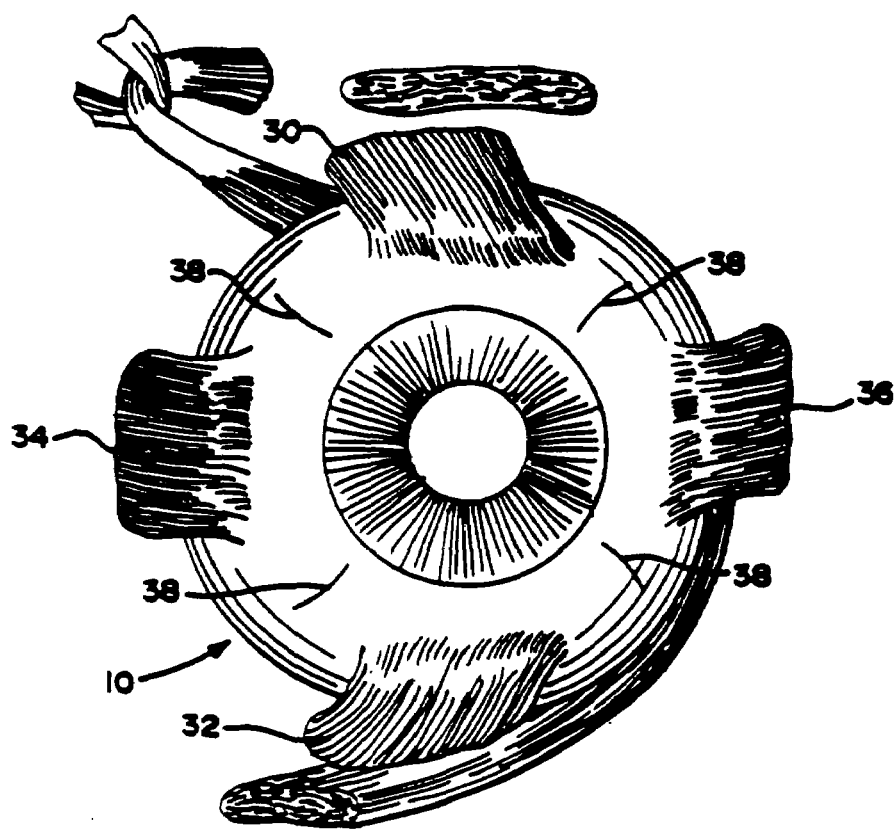
FIG. 2 is an anterior view of the eye showing the extrinsic eye muscles.

The incisions 38 are made radially outwardly from the cornea so as to generally bisect the area between the adjacent rectus muscles (e.g., between the superior and medial rectus muscles 30, 34 as shown by the incisions 38 in FIG. 2). For each incision 38, an initial incision is made to dissect to the conjunctiva 26, bypassing the Tenon's capsule 28. Then the incision is deepened to open the incision into the episclera, creating an incision of from 3 to 7 mm in length in the episclera. The incision is opened and, if necessary, the Tenon's capsule 28 is then moved laterally to expose the sclera 20.

The sclera 20 is then extended outwardly either mechanically with, e.g., a forceps, or by the application of a vacuum. A clip 40 is applied to the outwardly-extended sclera so as to put the sclera 20 under tension. The Tenon's capsule 28 is then reapposed over the clip and the conjunctiva 26 closed. No suturing is needed as the conjunctive self seals. The procedure is then repeated for each of the marked quadrants so that four clips are applied to the eye equally spaced about the cornea 24 between the adjacent rectus muscles.

FIG. 3 is a simplified drawing showing two clips 40 attached to the eye 10. The clips 40 grasp the sclera overlying the ciliary body 16 adjacent the iris 39. The applied clips 40 have a generally low profile, closely adhering to the curvature of the eye, thus providing reinforcement to the sclera.

With reference to FIGS. 4-9, the clips for use in the procedure can take many different forms. In general, it is contemplated that the clip 40 will have an overall dimension of approximately 1.5-2.5 mm in height (h), 0.4-0.6 mm in thickness (t) and no longer than 5.0-6.0 mm in length (l). The size of the clip is constrained by the distance between the adjacent rectus muscles. Specifically, the intent is to have the clip fit between the rectus muscles, so as to not impede the flow of blood to the eye through the arteries in the rectus muscles. Thus, instead of a single clip having a length of approximately 5.0 to 6.0 mm, a series of clips can be used the sum of whose total length fits between the adjacent rectus muscles. Of course, it is anticipated that the use of a single clip of the appropriate length will allow the procedure to be performed more easily and quickly.

As can be readily appreciated, the procedure can be simply reversed by merely again gaining access to the sclera by making an incision in the conjunctiva over the clip, moving the Tenon's capsule to expose the clip, and then removing the clip. No incision into the sclera is required.

In each of the FIGS. 4-9, the clip 40 includes two arms 42, 44 joined together for relative movement to each other. On the inside portions of the clip are teeth, serrations, spurs, barbs, fingers, points 46 or other structures or projections for engaging and securely holding or gripping the sclera to the arms of the clip as it is affixed to the sclera. The teeth 46 are sized to engage the sclera, but not be of a size or configuration to penetrate through the sclera (which might cause erosion of the sclera). Consequently, the teeth 46 may be as small as 20-80 μm. The clips are originally in their "open" position and then "closed" on the sclera with a forceps or other applicator, the clips remaining in their closed condition in the absence of an external force being applied to separate the arms of the clip. It is contemplated that the arms of the clips will be closed on the order of 10 to 15 degrees. This should prolapse the uvea and move the sclera outward approximately 0.5 mm, for a total of 2 mm if four clips are applied. This will increase the amplitude of accommodation, thus reversing the effects of presbyopia. This outward movement of the sclera should also increase the angle of the canals of Schlemn, thus increasing the aqueous flow and decreasing the intra-ocular pressure, to ameliorate the effects of glaucoma. The clips 40 may be made of any biocompatible material, including tantalum, polymethyl methacrylate (PMMA), and, preferably, titanium, that has sufficient deformability and resilience characteristics to permit the clip to be "opened" and then remain closed when applied to the sclera. Turning to FIG. 4, a first embodiment for the scleral clip 40 is shown in which each of the legs 42, 44 is bowed inward so as to impart some resiliency to the clip 40. Each leg 42, 44 also includes a series of teeth 46 for gripping into the sclera. The scleral clip of FIG. 5 is similar to that of FIG. 4, except resiliency is imparted to the clip 40 by having the legs 42, 44 bow outwardly.

FIG. 6 shows a further embodiment of a clip 40 that comprises a central portion in the shape of a rectangle folded along a diagonal, with a tooth 46 at each of the lower corners. A pair of staple-like members also having teeth 46 depend from the opposite ends of the rectangular portion so as to provide further means for gripping the sclera.

FIG. 7 illustrates a clip embodiment similar to FIGS. 3 and 4 except that the clip 40 includes a resilient band 48 that connects one leg to the other. The band 48 serves to keep tension on the legs 42, 44 of the clip when the teeth engage the sclera.

FIG. 8 shows a clip 40 that has a spider-like configuration with a plurality (4 shown) of legs depending from a central body, each leg terminating in a tooth 46.

FIG. 9 shows a clip 40 similar to those of FIGS. 3, 4 5 and 6, except that central portions of the clip 40 are removed to give it a fork-like appearance.

FIG. 10 is a further embodiment of a scleral clip 40 according to the present invention that is similar to the clip of FIG. 7, except that it does not include the resilient tensioning band. The clip 40 includes an indentation 50 in the center of each arm 42, 44 for cooperation with a tensioning instrument for application of the clip. Also, the teeth 46 have a length of 200 µm and are rounded, beveled, or blunted, so as to not present a sharp edge that could penetrate the sclera. The clip may be provided with a latex-free silicone polymer or acrylic coating, preferably white in color, on the outer or upper surface thereof in order to make the clip less conspicuous when attached to the eye.

FIGS. 11a and 11b are a perspective view and end view, respectively, of a further embodiment of a clip 40. This embodiment is similar to that in FIG. 4, except that the arms 42, 44 are not bowed, but are substantially flat. The clip 40 is preformed so that the angle between the two arms is approximately 175 degrees, so that, when applied to the sclera and the arms are closed 10 to 15 degrees, the angle between the arms is between approximately 160 to 165 degrees. This angle provides for a clip that, when applied more closely approximates the curvature of the eyeball. This is likely to be perceived by the wearer as more comfortable, and may also reduce any erosion of tissue that overlies the applied clip. The angle of the teeth 46 to their respective arms 42, 44 is approximately 90 degrees.

FIG. 12 is a perspective view of a clip 40 similar to that of FIGS. 11a, 11b, except that the end portions of the arms 42, 44 are relieved inwardly at 52. This reduces the portion of the clip 40 that, when attached to the eye, extends beyond the radius of curvature of the eye, to achieve the benefits of wearer comfort and reduction of tissue erosion discussed above.

FIG. 13 is a further embodiment of a clip 54 in accordance with the present invention. The clip 54 has the same overall dimensions as the clip disclosed above, i.e., approximately 3 to 5 mm by 5 to 6 mm, so as to fit between adjacent rectus muscles. However, the clip is oval or round in shape and has a central opening 56 enclosed by a continuous outer portion so that the clip 54 has a ring-like appearance. This clip is applied to the sclera by prolapsing the sclera through the central opening in the clip by mechanical means, such as a twist hook or forceps, or by the application of a vacuum. One or both of the central opening 56 or outer edge 58 may be provided with teeth 60, which are similar to teeth 46 described above, for securing the clip to the sclera. Further, the teeth may be bent out of the plane generally defined by the clip so that they more firmly grip the sclera. With reference to FIG. 14, the teeth on the outer edge or periphery 58 may be bent downwardly an angle α from between approximately 90 degrees to approximately 135 degrees, while the teeth on the central opening or inner periphery 56 are bent downwardly an angle β between approximately 20 degrees to 45 degrees.

The clip 54 is generally flat, with little or no angle between the two arms or sides 62, 64, as defined by the center line through the clip, thus providing a very low profile. Preferably, the clip 54 is sufficiently thin so that it conforms to the natural shape or curvature of the eye.

Thus, a method and a clip for performing the method have been provided that fully meet the objects of the present invention. While the invention has been described in terms of a preferred method and clip, there is no intent to limit the invention to the same. Instead, the invention is defined by the scope of the following claims.

What is claimed:

1. A method of treating glaucoma in a eye having a lens, ciliary muscles suspending the lens, sciera having a surface overlying the ciliary muscles and conjunctiva overlying the surface of the sciera comprising the steps of:

making an incision in the conjunctiva to gain access to the surface of the sclera overlying the ciliary muscle;
  exposing the sclera;
  providing a clip for attachment to the sclera so as to engage the surface thereof and provide external support;
  securing the clip to a portion of the sciera to effectively shorten the portion of the sciera held by the clip; and
  closing the conjunctiva over the clip.

2. The method of claim 1 wherein the sclera is supported by a clip at least two locations overlying the ciliary muscles.

3. The method of claim 1 wherein the sclera is supported by a clip at four locations substantially equally spaced about the lens.

4. The method of claims 3 wherein the sclera is supported by a clip that grips the sclera.

5. The method of claim 1 wherein a plurality of clips are applied to the sclera.

6. The method of claim 5 wherein at least four clips are applied to the sclera substantially equally spaced about the lens.

7. The method of claim 1 wherein the clip is attached to the sciera without making an incision in the sciera.

* * * * *

UNITED STATES PATENT AND TRADEMARK OFFICE
CERTIFICATE OF CORRECTION

PATENT NO. : 7,338,506 B2 Page 1 of 1
APPLICATION NO. : 10/250840
DATED : March 4, 2008
INVENTOR(S) : Nicholas C. Caro It is certified that error appears in the above-identified patent and that said Letters Patent is hereby corrected as shown below:

In Claim 1, Column 6, line 29, 31, 38 and 39 the word "sciera" should read --sclera--.

In Claim 7, Column 6, line 54 the word "sciera" should read --sclera--.

Signed and Sealed this

Tenth Day of June, 2008

JON W. DUDAS
*Director of the United States Patent and Trademark Office*